United States Patent [19]

Yeo et al.

[11] Patent Number: 4,758,239

[45] Date of Patent: * Jul. 19, 1988

[54] BREATHABLE BARRIER

[75] Inventors: Richard S. Yeo, Dunwoody; Daniel K. Schiffer, Marietta, both of Ga.

[73] Assignee: Kimberly-Clark Corporation, Neenah, Wis.

[*] Notice: The portion of the term of this patent subsequent to Dec. 15, 2004 has been disclaimed.

[21] Appl. No.: 926,033

[22] Filed: Oct. 31, 1986

[51] Int. Cl.$^4$ ............................................. A61F 13/16
[52] U.S. Cl. .................................... 604/366; 428/283; 428/284; 428/286; 428/290; 428/297; 428/298; 428/903; 428/913; 604/378
[58] Field of Search ............... 604/366, 378; 428/283, 428/284, 286, 297, 298, 903, 913, 290

[56] References Cited

U.S. PATENT DOCUMENTS

| | | | |
|---|---|---|---|
| 3,016,599 | 1/1962 | Perry, Jr. | 28/78 |
| 3,203,419 | 1/1963 | Joa | 128/290 |
| 3,156,242 | 11/1964 | Crowe | 128/296 |
| 3,253,715 | 5/1966 | Painter et al. | 210/504 |
| 3,426,754 | 2/1969 | Bierenbaum et al. | 128/156 |
| 3,518,041 | 6/1970 | Brelich | 8/115.7 |
| 3,590,585 | 7/1971 | DeWinter | 28/76 |
| 3,597,307 | 8/1971 | Paulusma et al. | 161/170 |
| 3,612,054 | 10/1971 | Matsuda et al. | 128/287 |
| 3,640,829 | 2/1972 | Elton | 260/2.5 AC |
| 3,679,538 | 7/1972 | Druin et al. | 161/159 |

(List continued on next page.)

FOREIGN PATENT DOCUMENTS

| | | |
|---|---|---|
| 0105629 | 4/1984 | European Pat. Off. . |
| 0141592 | 5/1985 | European Pat. Off. . |
| 0184392 | 11/1986 | European Pat. Off. . |
| 3417909 | 11/1985 | Fed. Rep. of Germany . |
| 57-142323 | 9/1982 | Japan . |
| 2103537 | 2/1983 | United Kingdom . |
| 2115702 | 10/1985 | United Kingdom . |

OTHER PUBLICATIONS

MONO-SOL 1-000 Series Hot Water Soluble Plastic Film data sheet (MONO-SOL Division, Chris Craft Industries, Inc., Gary, Indiana 46403).
"Resins, Water-Soluble," a chapter from Kirk-Othmer Encyclopedia of Chemical Technology, Third Edition, vol. 20, John Wiley and Sons, New York, 1982, pp. 207-230.
"Vinyl Polymers (Poly(Vinyl Alcohol))," a chapter in Kirk-Othmer Encyclopedia of Chemical Technology, Third Edition, vol. 23, John Wiley and Sons, New York, 1983, pp. 848-865.
VINOL Poly(Vinyl Alcohol) product line brochure, Air Products and Chemicals, Inc., Polymer Chemicals, Allentown, Pennsylvania 18105.
VINOL Poly(Vinyl Alcohol) product bulletin, Air Products and Chemicals, Inc., Polymer Chemicals, Allentown, Pennsylvania 18105.

Primary Examiner—James J. Bell
Attorney, Agent, or Firm—William E. Maycock

[57] ABSTRACT

A breathable barrier which includes:
A. a first layer which is a porous sheet having a first side and a second side; and
B. a second layer joined to the first side of the first layer, which second layer is a continuous film of a water-soluble polymeric material, in which:
 the film is not microporous in that it is substantially free of voids which connect the two surfaces of the film;
 water molecules are capable of being transported through the thickness of the film as a result of the solubility of the water molecules in the polymeric material; and
 the film has an average thickness of from about 3 to about 250 microns;
wherein the first layer side of the second layer is intimately comingled with at least some of the fibers at the surface of the first side of the first layer, none of the pores at the surface of the first side of the first layer are so large as to significantly adversely affect the barrier properties of the breathable barrier as a consequence of the comingling, and the breathable barrier has a water vapor transmission rate at 37 degrees C. and about 50 percent relative humidity of from about 100 to about 5,000 g/m²/24 hours and is impermeable to 0.9 percent by weight saline solution at about 21 degrees C. for a period of at least about one hour at a hydrostatic head of at least about 11.4 cm.

In place of a coating, the continuous film can be a preformed film of a water-soluble polymeric material which is laminated to the porous sheet. In preferred embodiments, the water-soluble polymeric material is a poly(vinyl alcohol) and the porous sheet is a meltblown nonwoven web. The disclosed breathable barriers are especially useful as outer covers and baffles in such disposable absorbent articles as diapers, sanitary napkins, and incontinent pads.

91 Claims, 4 Drawing Sheets

4,758,239

Page 2

U.S. PATENT DOCUMENTS

| | | | |
|---|---|---|---|
| 3,704,198 | 11/1972 | Prentice | 161/148 |
| 3,755,527 | 8/1973 | Keller et al. | 264/210 F |
| 3,843,761 | 10/1974 | Bierenbaum et al. | 264/41 |
| 3,849,241 | 11/1974 | Butin et al. | 156/167 |
| 3,869,310 | 3/1975 | Fukushima et al. | 264/49 |
| 3,870,593 | 3/1975 | Elton et al. | 260/2.5 AY |
| 3,891,487 | 6/1975 | Hoey | 156/78 |
| 3,932,682 | 1/1976 | Loft et al. | 428/296 |
| 4,006,052 | 2/1977 | Wang | 156/280 |
| 4,100,324 | 7/1978 | Anderson et al. | 428/280 |
| 4,178,271 | 12/1979 | Busch et al. | 204/159.12 |
| 4,197,148 | 4/1980 | Shinomura | 156/79 |
| 4,197,371 | 4/1980 | Holst et al. | 521/84 |
| 4,226,906 | 10/1980 | Jacob | 428/283 |
| 4,247,498 | 1/1981 | Castro | 264/28 |
| 4,257,997 | 3/1981 | Soehngen et al. | 264/145 |
| 4,289,832 | 9/1981 | Schwarz | 428/905 |
| 4,304,812 | 12/1981 | Perkins | 428/247 |
| 4,308,303 | 12/1981 | Mastroianni et al. | 428/90 |
| 4,347,844 | 9/1982 | Ohki et al. | 428/325 |
| 4,384,023 | 5/1983 | Okamura et al. | 428/338 |
| 4,415,617 | 11/1983 | D'Elia | 428/86 |
| 4,430,278 | 2/1984 | Jones, Sr. | 264/22 |
| 4,452,845 | 6/1984 | Lloyd et al. | 428/220 |
| 4,454,191 | 6/1984 | von Blucher et al. | 428/244 |
| 4,472,328 | 9/1984 | Sugimoto et al. | 264/22 |
| 4,519,909 | 5/1985 | Castro | 264/41 |
| 4,539,256 | 9/1985 | Shipman | 428/315.5 |
| 4,560,611 | 12/1985 | Naka et al. | 428/266 |
| 4,578,069 | 3/1986 | Whitehead et al. | 604/370 |
| 4,591,523 | 5/1986 | Thompson | 428/131 |
| 4,595,001 | 6/1986 | Potter et al. | 128/156 |
| 4,603,077 | 7/1986 | Fujimoto et al. | 428/289 |
| 4,608,111 | 8/1986 | Hume, III et al. | 156/327 |

BREATHABLE BARRIER

CROSS-REFERENCES TO RELATED APPLICATIONS

The use of a continuous film of a poly(vinyl alcohol) joined to a porous substrate having a controlled structure is described and claimed in copending and commonly assigned application Ser. No. 925,425 U.S. Pat. No. 4,713,068, entitled BREATHABLE CLOTH-LIKE BARRIER HAVING CONTROLLED STRUCTURE DEFENSIVE LAYER, filed of even date in the names of Kenneth Y. Wang and Richard S. Yeo, now U.S. Pat. No. 4,713,068. A barrier having at least three layers, one of which is a continuous film of a poly(vinyl alcohol), is described and claimed in copending and commonly assigned Application Ser. No. 925,332, entitled BREATHABLE, MULTILAYERED, CLOTHLIKE BARRIER, filed of even date in the names of Ralph V. Braun, Lance Garrett, Robert J. Phelan, and Richard S. Yeo. Finally, a baffle for a sanitary pad having a central zone of reduced water vapor permeability, which zone can result from a continuous film of a poly(vinyl alcohol) joined to the baffle material, is described and claimed in copending and commonly assigned Application Ser. No. 925,448, entitled BAFFLE HAVING ZONE WATER VAPOR PERMEABILITY, filed of even date in the names of Kenneth Y. Wang and Richard S. Yeo, now U.S. Pat. No. 4,713,069.

BACKGROUND OF THE INVENTION

The present invention relates to a breathable barrier, i.e., a structure which is substantially impervious to liquid water but permeable by water vapor. More particularly, the present invention relates to a breathable barrier which is a porous sheet, such as a nonwoven web, coated with poly(vinyl alcohol) or laminated to a poly(vinyl alcohol) film.

Absorbent articles, especially disposable absorbent articles such as diapers, sanitary napkins, bedpads, incontinent pads, and the like are well known and important items of commerce. Such articles are capable of absorbing and retaining liquid discharges from the body. They typically have an outer cover or baffle of a liquid-impermeable plastic film, such as a polyethylene or polypropylene film, to prevent retained liquid from leaking from the article and soiling items of clothing, bedding, furniture, and the like.

Such liquid-impermeable film prevents, or at least minimizes, leakage by establishing a barrier to the passage of liquid from the absorbent article in situations where either the capacity of the absorbent article has been exceeded or the loading of the target zone exceeded the capacity of the absorbent article to wick liquid from the target zone to storage areas.

Such film, however, suffers from several disadvantages. Because the film is impermeable to both liquid and water vapor, the absorbent article feels hot when dry and clammy when wet. Such clammy state can cause irritation of the skin and even severe dermatological problems, such as diaper rash on infants wearing disposable diapers which have been left on too long. In fact, diaper rash can develop relatively quickly because of illness or changes in diet. In addition, the plastic film employed as the outer cover or baffle is severely lacking in aesthetic qualities, especially for such products as disposable diapers.

One proposal for the elimination of such disadvantages is the use of a breathable, liquid impermeable barrier as the outer cover or baffle. As used herein, the term "breathable" means that the carrier is pervious to water vapor; that is, water vapor will pass through the barrier. While considerable progress has been made in the development of breathable films, such materials typically are lacking in aesthetic qualities.

Various breathable outer coverings or other materials are known. For example, U.S. Pat. No. 3,156,242 discloses a flexible absorbent sheet which is useful as a surgical dressing. The backing sheet or outer layer of the dressing is either air pervious by nature, such as a microporous film, or has had holes or slits formed in it. The example employed a perforated polyethylene film.

U.S. Pat. No. 3,426,754 teaches a breathable medical dressing. Such dressing comprises a backing having an open-celled structure, preferably coated with a continuous layer of a microporous pressure-sensitive adhesive. The backing employs a plastic film to which the desired properties have been imparted as a result of special processing conditions. The film typically can be prepared from polyolefins, polyacetals, polymethylene sulfide, polyethylene sulfide, polyphenylene oxide, polyamides, polyesters, and the like. The film possesses an open-celled structure, the voids of which are accessible to the outside surface by means of passageways which generally are under 5,000 Angstroms, e.g., from 100 to 5,000 Angstroms. In addition, such film has a final crystallinity of at least 40 percent.

A porous sheet and a process for making it are described in U.S. Pat. No. 4,347,844. The sheet is reported to be useful as a water-impermeable, vapor-permeable backing sheet for disposable diapers. The sheet contains a filler, the particles of which have been broken by the application of a compressive force to cause the formation of voids or spaces, i.e., micropores, which permit the passage of water vapor through the sheet while acting as a barrier to liquid water. The sheet apparently can be made of a nonfoamed thermoplastic resin, such as polyethylene and nylon. In addition, the patent suggests that the film can be a composite of a polyethylene or nylon film and spunbonded polyethylene or polyester. The use of a spunbonded material alone does not appear to be within the scope of the disclosure.

Another type of microporous film is described in U.K. Pat. No. GB 2,115,702B. The patent is directed toward an absorbent article, such as a disposable diaper or sanitary napkin, in which the article has a vapor-permeable, liquid-impermeable backing sheet. The backing sheet is composed of a film produced by mixing 100 parts by weight of a polyolefin resin, 28 to 200 parts by weight of a filler, and 10 to 70 parts by weight of a liquid or wax-like hydrocarbon polymer, molding the mixture to form a film, and then stretching the film laterally and/or longitudinally until it has a dimension of more than 1.2 times its original dimension in that direction, thereby resulting in the formation of fine pores in the film. Examples of polyolefins include polyethylene and polypropylene. A variety of fillers can be used, and examples of the hydrocarbon polymer include liquid polybutadienes, liquid polybutenes, and hydrogenates of liquid polybutadienes, among which saturated polyhydroxy-substituted hydrocarbons obtained by hydrogenating hydroxy-terminated liquid polybutadienes are preferred. See also U.S. Pat. No. 3,870,593 which describes stretching a film containing finely divided particles of a nonhygroscopic inorganic salt, such as calcium carbonate, in order to obtain a microporous film. The microporous sheet material described in U.S. Pat. No. 3,640,829 also involves incorporating within the polymer an inorganic salt which is leached out to produce the micropores.

U.S. Pat. No. 4,591,523 relates to an apertured, macroscopically expanded, three-dimensional polymeric web exhibiting breathability and resistance to fluid transmission. The web is reported to have particular utility as a breathable barrier for a disposable diaper. The web preferably comprises a deeply drawn three-dimensional structure containing a multiplicity of debossments of macroscopic cross-section (i.e., visibly perceivable by the normal human eye at a perpendicular distance of about one foot), each of said debossments originating as an aperture in a first surface of the web and having a continuously interconnected side wall extending in the direction of a second, remotely located parallel surface of the web. The side wall of each debossment terminates to form an end wall in the second surface of the web. The end wall includes a multiplicity of apertures, each of said apertures being sized and shaped to independently support an aqueous fluid meniscus. These smaller apertures in each end wall are so spaced relative to all adjacent apertures in the end wall that the aqueous fluid menisci supported in the apertures do not contact one another.

Waterproof products capable of transmitting air and water vapor which have fabric-like aesthetic properties are described in U.S. Pat. No. 3,932,682. The products are made by spray-spinning filamentary material directly onto an open-celled microporous polymer film, such that thermal self-bonding occurs between the filamentary material and the film or by spray-spinning the filamentary material in the same manner onto an elastic film, stretching the resulting product until an open-celled structure is produced in the film portion of the product and thereafter heating or heat setting the resulting product at substantially constant length to impart dimensional stability thereto. Polymers suitable for making films appear to be those described in U.S. Pat. No. 3,426,754, discussed hereinabove. As already noted, the filamentary material is produced by spray-spinning, i.e., meltblowing, directly onto the film.

U.S. Pat. No. 4,308,303 describes a flocked, foam-coated, fibrous-reinforced, water vapor permeable barrier having the appearance of fabric and capable of filtering bacteria. The barrier comprises a microporous polyolefin film coated on at least one surface with a foamed latex polymer, flocked fibers on the exterior surface of said foamed latex polymer, and a web of spunbonded fibers on the exterior surface of the flocked, foamed latex polymer. The film is rendered microporous by stretching a film which contains minute fracture sites or pore-nucleating agents such as finely divided filler and/or minute crystalline domains. The use of a finely divided, inorganic, water-insoluble, inert filler such as calcium carbonate having an average particle size of less than 3 microns is preferred.

U.S. Pat. No. 4,560,611 relates to a moisture-permeable, waterproof coated fabric. Briefly, a microporous polyurethane layer is formed on a base fabric which may be knitted, woven, nonwoven, or the like. The coating solution consists of a polar organic solvent solution containing 8 to 25 percent by weight of a polyurethane elastomer, 0.1 to 10 percent by weight of a water repellent agent, 0.2 to 3 percent by weight of a polyisocyanate, and 1 to 8 percent by weight of a nonionic surfactant. The water repellent agent typically is a fluorine- or silicone-based material. The polyisocyanate usually will be any of the well known di- or triisocyanates. The polyurethane elastomer can be a polyester or polyether polyurethane.

A somewhat similar approach is described in European Patent Application No. 85308671.8, Publication No. 0 184 392 A2. A waterproof, moisture-vapor permeable unitary sheet material comprises a microporous polymeric matrix having pores comprising continuous passages extending through its thickness and opening into the opposite surfaces thereof, the passages being sufficiently filled with a moisture-vapor permeable, water-impermeable, hydrophilic material to prevent the passage of water and other liquids through the unitary sheet material while readily permitting moisture vapor transmission therethrough, thereby rendering the sheet material breathable. Preferably, the average pore size will be less than about 10 percent of the thickness of the matrix. By way of example, the average pore size for a matrix having a thickness of about 10 to 50 micrometers typically will be on the order of 1 to 5 micrometers or less. By contrast, the average pore size or opening of a woven fabric is about the same magnitude as its thickness. A matrix having too large a pore size will permit the passage of water therethrough as hydrophilic material solidified therein will not sufficiently close the pores against the passage of liquid. The matrix can be prepared by known methods from any polymeric material which is substantially impenetrable by water. Suitable polymeric materials include polyolefins, polyesters, polyamides, and the like. The preferred hydrophilic material is polyethylene oxide which preferably is polymerized with a polyisocyanate to give a polyurethane.

U.S. Pat. No. 4,197,371 discloses a water vapor absorbing and transmitting sheet material. The sheet material comprises a natural or synthetic rubber or a rubber-like polymer having uniformly incorporated therein particles of at least one swellable modified polymer. Examples of suitable swellable modified polymers include, among others, modified starches and celluloses. Apparently, such sheet materials are not suitable for use as an outer cover for a disposable absorbent product, e.g., a diaper or sanitary napkin. See also U.S. Pat. No. 4,178,271 which describes a similar sheet material based on a sheet-like structure of poly(vinyl chloride) or a copolymer of vinyl chloride.

U.S. Pat. No. 3,869,310 describes flexible sheet materials which are leather-like. Although the materials allegedly have improved physical properties, particular properties, such as water vapor permeability, are not discussed. The materials comprise a nonwoven fibrous mat and a polymeric impregnant which has a porous structure and is substantially not bonded to the fibers of the mat. The materials are obtained by preparing a nonwoven fibrous mat composed of fibers prepared from at least two different polymeric materials, impregnating the mat with a first liquid which is a solvent for one of the polymeric materials and a nonsolvent for the other polymeric materials, dissolving the fibers composed of the polymeric material which is soluble in the liquid, and coagulating the polymer solution resulting from the addition of the first liquid into a porous polymeric structure which is substantially not bonded to the undissolved fibers by the addition of a second liquid which is a nonsolvent for all of the polymeric materials originally present in the nonwoven fibrous mat but which is at least partially miscible with the first liquid. The list of suitable polymeric materials which can be employed includes poly(vinyl alcohol), although the preferred combinations of polymeric materials apparently are nylon-6 and polystyrene, nylon-6 and polypropylene, poly(ethylene terephthalate) and polystyrene, poly(vinyl chloride) and polypropylene, nylon-6 and poly(vinyl acetate), and nylon-6 and a polyurethane elastomer. One example, however, involved the use of a nonwoven mat composed of fibers of poly(vinyl chloride) and poly(vinyl alcohol); the first liquid was N,N-dimethylformamide which is a solvent for poly(vinyl alcohol) but a nonsolvent for poly(vinyl chloride).

The use of poly(vinyl alcohol) as a binder for a nonwoven fabric is described in U.S. Pat. No. 3,518,041. The nonwoven fabric is composed of cellulosic fibers alone or in combination with other natural or synthetic fibers. The binder is a poly(vinyl alcohol) resin in film, powder, fiber, or other particulate form which is crosslinked in situ with formaldehyde. The binder is applied to the fabric as an aqueous solution or poly(vinyl alcohol) fibers may be incorporated into the fabric and activated by treating the fabric with water. The fabric then is treated with an aqueous solution of formaldehyde which contains a catalyst.

A disclosure somewhat similar to that of the above patent is found in U.S. Pat. No. 3,253,715 which describes boil-proof nonwoven filter media. The media are prepared by treating a multilayered nonwoven fabric with a binder which is an aqueous solution of poly(vinyl alcohol) and a polyacrylic acid or crosslinked polyacrylic acid.

It is interesting to note that, in contrast to U.S. Pat. Nos. 3,518,041 and 3,253,715, U.S. Pat. No. 3,590,585 describes a composite structure, useful as an artificial seaweed, which employs water-decomposable poly(vinyl alcohol) filaments to temporarily hold buoyant, water-resistant strands in place during handling, transporting, and installing of the product. Also of interest in this regard is U.S. Pat. No. 4,304,812 which describes the backcoating of an open-weave fabric. Prior to the backcoating step, a temporary protective coating is applied to the face of the fabric. After backcoating the fabric, the protective coating is removed with a solvent medium. Suitable protective coatings preferably are at least partially water soluble and include water-soluble poly(vinyl alcohol) or partially hydrolyzed poly(vinyl acetate).

U.S. Pat. No. 3,597,307 describes a supple sheet material which is composed of a fibrous nonwoven web and a polyurethane filler. The fibers of the web can be prepared from poly(vinyl alcohol) and the amount of the filler can be up to 30 percent by weight, based on the weight of the sheet material. Although the sheet material is stated to have a good water vapor pick-up value, it is not known if the material is permeable to water vapor. See also U.S. Pat. No. 4,006,052.

U.S. Pat. No. 3,891,487 discloses a decorative laminate which has a textile backing, a crushed, thermoset plastic foam bonded thereto, and a transparent polymeric film overlaying the foam. The film preferably is cast from a latex; suitable materials for preparing the latex include poly(vinyl alcohol). The film can be made breathable by mechanically foaming the latex before casting, mechanically puncturing the film, using chemical blowing agents, or dissolving or digesting out temporary fillers placed in the latex before it is cast. The textile backing apparently can be either woven or nonwoven. The decorative laminate is useful as, for example, a simulated oil painting, and clearly is not intended to be contacted by water.

Microporous coated fabrics are described in U.S. Pat. No. 4,226,906. Microporosity apparently results from the use of clustered microspheres. The microspheres may be synthetic or naturally occurring. If the former, they are prepared by bonding individual microspheres in a matrix which is insoluble in the coating composition; the bonding agent for such matrix can be, for example, poly(vinyl alcohol). However, the patent does not appear to teach the use of poly(vinyl alcohol) in the preparation of microporous coated fabrics when naturally occurring microspheres are used; in such case, the coating composition was based on poly(vinyl chloride) and the fabric was a nonwoven polyester.

U.S. Pat. No. 4,415,617 discloses a base fabric for the manufacture of embroidery and lace. The base fabric is a nonwoven web of poly(vinyl alcohol) fibers which has been processed in such a manner as to convert one surface of the web into a gas-permeable film comprising thermoplasticized and rehardened, flattened fibers and portions of fibers. The base fabric then can be dissolved away from embroidery stitched thereon by exposing the fabric to water at a temperature of about 100 degrees C.

U.S. Pat. No. 4,454,191 describes a waterproof and moisture conducting fabric coated with a hydrophilic polymer. The fabric can be a woven, knit, felt, or nonwoven material which is composed of natural, synthetic, or mineral fibers. The fabric itself must be permeable to water vapor. The fabric is sealed with a hydrophilic polymer which is capable of absorbing, transporting, and releasing water molecules. Such capability results from the presence in the polymer of hydrophilic groups, such as hydroxy, amino, ether, and carboxy groups. Thus, suitable polymers include those prepared from hydroxyalkyl acrylates, the acrylic or methacrylic esters of polyalkylene oxides or polyalkylenimides, and the like. Other suitable polymers include modified vinyl alcohol resins, regenerated cellulose, a poly(vinyl chloride) having built-in monomers which have powerful hydrophilic groups, copolymerizates of vinyl chloride and vinyl acetate in which the acetate groups have been hydrolyzed to hydroxy groups, and polyurethanes having excess hydroxy or amino groups.

A somewhat related disclosure is found in German Published Patent Application No. 3417909 A1, which describes the use of a water-soluble poly(vinyl alcohol) film in the resorbent material of a sanitary pad. The film reportedly prevents soiling of clothing while permitting sanitary disposal of the used article. There appears to be no mention of the characteristics of the film or where and how the film is placed in the pad.

It perhaps should be mentioned that there is a relatively large body of literature on the preparation of microporous films, only a relatively small portion of which has been discussed hereinabove. While a detailed discussion of such body of literature is beyond the scope of this section, a limited number of additional, representative references perhaps should be mentioned for the sake of completeness. Such references include, by way of illustration only, U.S. Pat. Nos. 4,247,498, 4,519,909, 4,257,997, 4,452,845, 4,539,256, 3,843,761, 3,679,538, 4,430,278, 4,289,832, 4,384,023, 4,472,328, 4,197,148, U.K. Published Patent Application No. GB 2,103,537A, Japanese Published Patent Application No. 57-142323, and European Patent Application Nos. 84307198.6, Publication No. 0 141 592 A2, and 83305161.8, Publication No. 0 105 629 A2.

Although various of the breathable barriers described above have proven useful in such absorbent articles as disposable diapers and sanitary napkins, there still is a need for an effective breathable outer cover or baffle which has a clothlike feel and can be manufactured cheaply in large quantities.

SUMMARY OF THE INVENTION

It therefore is an object of the present invention to provide a breathable barrier.

Another object of the present invention is to provide a breathable barrier which is suitable for use as an outer cover or baffle for a disposable absorbent article.

A further object of the present invention is to provide a breathable barrier which is clothlike in appearance and feel.

These and other objects will be apparent to one having ordinary skill in the art from a reading of the specification and claims which follow.

Accordingly, the present invention provides a breathable barrier which comprises:
  A. a first layer which is a porous sheet having a first side and a second side; and
  B. a second layer joined to said first side of said first layer, which second layer comprises a continuous film of a water-soluble polymeric material, in which:
    said film is not microporous in that it is substantially free of voids which connect the two surfaces of said film;
    water molecules are capable of being transported through the thickness of said film as a result of the solubility of said water molecules in said polymeric material; and
    said film has an average thickness of from about 3 to about 250 microns;
wherein the first layer side of said second layer is intimately comingled with at least some of the fibers at the surface of said first side of said first layer, none of the pores at the surface of said first side of said first layer are so large as to significantly adversely affect the barrier properties of said breathable barrier as a consequence of said comingling, and said breathable barrier has a water vapor transmission rate of 37 degrees C. and about 50 percent relative humidity of from about 100 to about 5,000 g/m$^2$/24 hours and is impermeable to 0.9 percent by weight saline solution at about 21 degrees C. for a period of at least about one hour at a hydrostatic head of at least about 11.4 cm.

The present invention also provides a breathable barrier which comprises a porous sheet laminated on at least one side to a film of a water-soluble polymeric material, in which:
  said film is not microporous in that it is substantially free of voids which connect the two surfaces of said film;
  water molecules are capable of being transported through the thickness of said film as a result of the solubility of said water molecules in said polymeric material; and
  said film has an average thickness of from about 3 to about 250 microns;
wherein sad breathable barrier has a water vapor transmission rate at 37 degrees C. and about 50 percent relative humidity of from about 100 to about 5,000 g/m$^2$/24 hours and is impermeable to 0.9 percent by weight saline solution at about 21 degrees C. for a period of at least about one hour at a hydrostatic head of at least about 11.4 cm.

The present invention still further provides a breathable barrier which comprises:
  A. a first layer which is a porous sheet having a first side and a second side; and
  B. a second layer joined to said first side of said first layer, which second layer comprises a continuous film of a poly(vinyl alcohol), in which:
    said film is not microporous in that it is substantially free of voids which connect the two surfaces of said film; and
    said film has an average thickness of from about 3 to about 250 microns;
wherein the first layer side of said second layer is intimately comingled with at least some of the fibers at the surface of said first side of said first layer, none of the pores at the surface of said first side of said first layer are so large as to significantly adversely affect the barrier properties of said breathable barrier as a consequence of said comingling, and said breathable barrier has a water vapor transmission rate at 37 degrees C. and about 50 percent humidity of from about 100 to about 5,000 g/m$^2$/24 hours and is impermeable to 0.9 percent by weight saline solution at about 21 degrees C. for a period of at least about one hour at a hydrostatic head of at least about 11.4 cm.

The present invention yet further provides a breathable barrier which comprises a porous sheet laminated on at least one side to a film of a poly(vinyl alcohol), in which:
  said film is not microporous in that it is substantially free of voids which connect the two surfaces of said film; and
  said film has an average thickness of from about 3 to about 250 microns;
wherein said breathable barrier has a water vapor transmission rate at 37 degrees C. and about 50 percent relative humidity of from about 100 to about 5,000 g/m$^2$/24 hours and is impermeable to 0.9 percent by weight saline solution at about 21 degrees C. for a period of at least about one hour at a hydrostatic head of at least about 11.4 cm.

In preferred embodiments, the porous sheet or first layer is a nonwoven web. In other preferred embodiments, the porous sheet is a meltblown or spunbonded web. In still other preferred embodiments, the porous sheet is a meltblown or spunbonded web which is composed of polyolefin fibers, e.g., polyethylene or polypropylene fibers. In yet other preferred embodiments, the film of a water-soluble polymeric material or second layer is substantially insoluble in water having a temperature less than about 50 degrees C.

The present invention additionally provides a multilayer absorbent article in which at least one layer is a breathable barrier as described and claimed herein.

In preferred embodiments, the absorbent article is a disposable diaper, a sanitary napkin, or an incontinent pad.

DETAILED DESCRIPTION OF THE INVENTION

As used herein, the term "breathable barrier" means a material which is permeable to water vapor as measured by the water vapor transmission rate at 37 degrees C. and about 50 percent relative humidity, but which is impermeable to 0.9 percent by weight of saline solution at about 21 degrees C. for a period of at least about one hour at a hydrostatic head of at least about 11.4 cm. The material is permeable to water vapor for the purposes of the present invention if it has a water vapor transmission rate at 37 degrees C. and about 50 percent relative humidity of from about 100 to about 5,000 g/m²/24 hours.

As a matter of convenience, the terms "porous sheet" and "first layer" are used interchangeably throughout this specification, with occasional cross-referencing. The same is true of the terms "continuous film" or "film" or variations thereof and "second layer."

In the broadest interpretation of the present invention, the porous sheet or first layer can be any porous material which is desired to be converted to a breathable barrier. Thus, such porous sheet can be a paper substrate, woven web, knitted fabric, spunlaced material, bonded carded web, needle punched material, stitch bonded fabric, meltblown web, spunbonded web, coformed web, or the like. Preferably, however, the porous sheet will be a nonwoven web. Most preferably, the porous sheet will be a spunbonded, meltblown, or coformed nonwoven web.

Various methods for making porous sheets are, of course, well known to those having ordinary skill in the art and need not be discussed herein. For the most preferred porous sheets, however, representative methods are described in, for example, U.S. Pat. Nos. 3,016,599, 3,755,527, 3,704,198, 3,849,241, and 4,100,324, and 3,692,618, all of which are incorporated herein by reference. With respect to coformed webs, it perhaps should be noted that the web in general will consist of primary web-forming fibers with secondary fibers or particles dispersed therein.

The material from which the porous sheet is prepared is not known to be critical, provided that there is sufficient adhesion between the porous sheet and the polymeric material. That is, the second layer must be joined to the first layer. Moreover, it should be appreciated by one having ordinary skill in the art that the levels of adhesion for any given porous sheet may differ, depending upon the nature of the polymeric material and whether it is applied as a solution or as a preformed film. Although the use of a supplemental adhesive, i.e., an adhesive material different from the polymeric material, is contemplated and comes within the scope of the present invention, such use is not preferred. In any case, whether or not adhesion is sufficient for any given combination of porous sheet material and polymeric material is readily determined by one having ordinary skill in the art without a need for undue experimentation. Moreover, when insufficient adhesion is observed, one having ordinary skill in the art, following the guidelines contained herein, can easily determine conditions under which sufficient adhesion will be achieved.

When the porous sheet is a nonwoven web, the preferred materials for the preparation of the web are polyolefins. For the purposes of the present disclosure, the term "polyolefin" is meant to include any polymeric material a major constituent of which, i.e., at least 50 percent by weight, is a polyolefin. Thus, the term includes homopolymers, copolymers, and polymer blends.

Copolymers can be random or block copolymers of two or more polyolefins (or two or more different polyolefin monomeric precursors) or of one or more polyolefins and one or more nonpolyolefin polymers. Similarly, polymer blends can utilize two or more polyolefins or one or more nonpolyolefin polymers. As a practical matter, homopolymers and copolymers and polymer blends involving only polyolefins are preferred, with homopolymers being most preferred.

Examples of polyolefins include polyethylene, polystyrene, poly(vinyl chloride), poly(vinyl acetate), poly(vinylidene chloride), poly(acrylic acid), poly(methacrylic acid), poly(methyl methacrylate), poly(ethyl acrylate), polyacrylamide, polyacrylonitrile, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, and the like.

The preferred polyolefins are those prepared from unsaturated hydrocarbon monomers, with polyethylene and polypropylene being most preferred.

The size and thickness of the porous sheet are not critical. However, those having ordinary skill in the art should appreciate that it may be necessary to alter film thicknesses or materials if very thin or very thick porous sheets are employed. The present invention is unique in part because it permits the use of relatively thin films or second layers without sacrificing barrier properties. Thus, one goal of the present invention is to keep the films relatively thin. Thus, some experimentation may be required to optimize the performance of the resulting breathable barrier upon changing the thickness of the porous sheet or first layer. In addition, some porous sheets may exhibit partial barrier characteristics to liquid water, which characteristics should be taken into consideration when planning film thicknesses. In fact, the presence of such characteristics in the first layer is both desirable and preferred.

By way of illustration, satisfactory breathable barriers have been prepared using nonwoven spunbonded or meltblown porous sheets as first layers. Spunbonded basis weights have varied from about 13.6 to about 102 g per square meter, or $g/m^2$, and meltblown basis weights have varied from about 3.4 to about 102 $g/m^2$.

As already stated, the second layer is a continuous film of a water-soluble polymeric material. Such film can be a preformed film which is joined or laminated to the porous sheet or first layer by any suitable method known by those having ordinary skill in the art, such as thermal bonding, chemical or adhesive bonding, solvent bonding, ultrasonic bonding, and the like. Of course, the joining method should not significantly adversely affect the solubility of water molecules in the film or the barrier properties of either the film or the porous sheet. Alternatively, and preferably, the second layer of continuous film can be formed in situ from an aqueous coating on the porous sheet or first layer. Because the in situ formation of the second layer is preferred, most of the discussion which follows is directed thereto.

When the continuous film or second layer is formed in situ on the porous sheet or first layer, the structure of the porous sheet, e.g., the sizes of the pores at the surface of the porous sheet on which the film will be formed, is of concern only in the sense that none of such pores can be so large as to interfere with the formation of the continuous film in such a manner as to significantly adversely affect the barrier properties of the breathable barrier. It is important to note that perfection is not required; it is necessary only that those film imperfections which are present do not result in a significant deterioration of the barrier properties, especially with respect to liquid water.

In the case of the most preferred porous sheet, i.e., a meltblown web, it is estimated that, in order to obtain generally satisfactory barrier properties, each of at least about 50 percent of the pores at the surface to be coated of the meltblown porous sheet should have a cross-sectional area of less than about $3.2 \times 10^{-8} m^2$, with none of such pores being so large as to prevent the formation of the continuous film in such a manner as to significantly adversely affect the barrier properties of the breathable barrier. Moreover, it is believed that optimum barrier properties should be possible with meltblown webs when essentially none of the pores at such surface has a cross-sectional area in excess of about $3.2 \times 10^{-8} m^2$. Because of the numerous combinations of porous sheets and water-soluble polymeric materials which are possible, however, it is not feasible to do more than offer the foregoing guidelines with respect to the pore size distribution of the porous sheet.

When the polymeric material is applied to the porous sheet as an aqueous solution to form a continuous film in situ, it must, of course, be capable of forming a continuous film under the conditions of application. In general, the polymeric material can be any water-soluble polymeric material which, in addition to the foregoing requirement, will form a film which:

is not microporous in that it is substantially free of voids which connect the two surfaces of the film;
is capable of transporting water molecules through the thickness of the film as a result of the solubility of said water molecules in the polymeric material; and has an average thickness of from about 3 to about 250 microns.

These film characteristics also apply to the preformed film which is laminated to the porous sheet.

An important aspect of the present invention is the fact that a film employed herein, whether preformed or formed in situ, is not a microporous film as that term has been used in the art. That is, a film utilized in the present invention does not have voids or micropores which connect the two surfaces of the film. In a microporous film, the interconnecting voids provide a pathway for the transport of water molecules from one surface to another, the driving force being the differences in relative humidities at the two surfaces. A film employed in the present invention, however, utilizes a different mechanism, namely: water molecules must be soluble in the film and capable of being transported by means of such solubility from one surface of the film to the other.

As already noted, the average thickness of the second layer should be in the range of from about 3 to about 250 microns. Preferably, the average thickness of the second layer will be in the range of from about 3 to about 100 microns, more preferably from about 3.4 to about 50 microns, and most preferably from about 5 to about 25 microns.

If a third layer is present which also is a continuous film of a water-soluble polymeric material, and the third layer is joined to the second layer, than both the second and third layer thicknesses can be reduced. Under these conditions, the preferred range for the thicknesses of each such layer is from about 1.5 to about 85 microns, with a range of from about 1.5 to about 12 microns being more preferred. The most preferred thickness range for each of the two adjacent film layers is from about 1.5 to about 10 microns.

It should be noted that average film thickness is involved, not maximum film thickness. Because of the inherent relative roughness of the surfaces of many porous sheets, and nonwoven webs in particular, film thickness typically varies over the area constituting the second layer. This necessitates dealing with average film thickness. Moreover, the average film thickness is an adequate measure of the amount of the continuous film which constitutes the second layer. Stated differently, some variability or imprecision in film thickness is acceptable since the barrier properties of the film do not appear to be extremely sensitive to film thickness.

A related problem is the difficulty of accurately measuring film thickness, unless the film is preformed. For the purposes of the present invention, it is sufficient if film thickness is only estimated. A reasonable estimate of the thickness of a film can be made from the amount of add-on of the PVOH resin or PVOH composition if the density of the resin or composition is known. With the poly(vinyl alcohol) resins employed in the examples, it was found that each $g/m^2$ of add-on was approximately equivalent to 0.85 micron of film thickness.

In general, the water-soluble polymeric materials suitable for use in the present invention can be either natural or synthetic, and the former group of materials can be modified, if desired, to achieve particular properties. The natural and modified natural materials included, by way of illustration only, agar, carragenan, corn starch, guar gum, gum arabic, gum karaya, gun tragacanth, locust bean gum, potato starch, wheat starch, rice starch, tapioca, casein, gelatin, pectin, sodium alginate, xanthan gum, aminoalkyl starches, dextran, hydroxyalkyl starches, hydroxyethyl cellulose, hydroxypropyl cellulose, methyl cellulose, sodium carboxymethyl cellulose, and the like.

Examples of synthetic water-soluble polymeric resins include poly(vinyl alcohol), polyacrylamides, poly(acrylic acid), poly(methacrylic acid), polyethyleneimine, Mannichsubstituted polyacrylamides, poly(dimethylaminoethyl methacrylate), polyalkylene polyamines, poly(vinylbenzyltrimethylammonium chloride), poly(diallyldimethylammonium chloride), poly(glycidyltrimethylammonium chloride), poly(ethylene oxide), poly(N-vinyl-2-pyrrolidinone), methyl vinyl ether-maleic anhydride copolymers and lower alkyl esters thereof, and the like.

In many cases, it may be necessary to include a crosslinking agent in order to obtain the requisite film properties. However, suitable crosslinking agents and their uses are well known to those having ordinary skill in the art.

The use of synthetic water-soluble materials is preferred, with poly(vinyl alcohol) being most preferred. Because poly(vinyl alcohol) is most preferred and was used in the examples, the material and its use are described in greater detail below. However, such description is not to be construed as in any way limiting either the spirit or the scope of the present invention.

As is well known in the art, poly(vinyl alcohol), from which the second layer most preferably is prepared, is a synthetic water-soluble polymeric material. There are, however, numerous grades of poly(vinyl alcohol), many of which have different solubility characteristics in water. For example, some grades are soluble in water at ambient temperature, while others are soluble in water only at elevated temperatures. At the present time, though, there are no known limitations with respect to the grade or nature of the poly(vinyl alcohol) employed in the preparation of the second layer.

Poly(vinyl alcohol), for convenience often referred to hereinafter as PVOH, is produced by the hydrolysis of poly(vinyl acetate). PVOH is available commercially in several grades which differ in degree of polymerization and degree of hydrolysis. In general, the degree of polymerization will vary from about 500 to about 2,500; the corresponding molecular weights are from about 22,000 to about 110,000. The degree of hydrolysis usually will vary from about 85 percent to essentially 100 percent (e.g., 99.7 percent minimum hydrolysis). In addition, some modified PVOH materials also are available, such as so-called tackified grades which are borated PVOH resins (see U.S. Pat. No. 3,135,648).

Typical of the commercially available PVOH resins are the VINOL ® resins available from Air Products and Chemicals, Inc., Polymer Chemicals, Allentown, Pa. Preformed PVOH films also are commercially available, such as the MONO-SOL ® 1-100 series from Mono-Sol Division, Chris Craft Industries, Gary, Ind.

Preferably, the PVOH resin will have a relatively high degree of hydrolysis, typically essentially completely hydrolyzed, since such a resin does not require the use of a crosslinking agent.

Although resins having a lower degree of hydrolysis can be employed with satisfactory results, such resins may require the addition of a crosslinking agent in the aqueous solution of PVOH with which the porous sheet is coated, depending upon the use intended for the breathable barrier, since such resins often are quite soluble in water at ambient temperature. However, inclusion of a crosslinking agent is not required, even for such resins.

One of the remarkable aspects of the present invention is the fact that such resins can be used to prepare satisfactory breathable barriers. There are a number of porous sheets, meltblown webs in particular, which exhibit barrier properties with respect to liquid water. Such barrier properties, however, generally are insufficient to permit such porous sheets to serve by themselves as breathable barriers having the properties associated with the barriers of the present invention. Nevertheless, such sheets, when joined with a continuous film of a water-soluble polymeric material as provided herein, yield barriers having properties which exceed the sum of the properties of the individual components making up the barrier. That is, there is a kind of synergy which results from the combination of a porous sheet having significant barrier properties with a continuous film of a water-soluble polymeric material as provided by the present invention. For some applications, the porous sheet permits the use of polymeric materials which are quite soluble in water at ambient temperature. As a practical matter, however, it is preferred that such continuous film is substantially insoluble in water having a temperature less than about 50 degrees C.

Suitable crosslinking agents are those known in the art, such as glyoxal; formaldehyde; urea-formaldehydes; melamine-formaldehydes; metal compounds, such as cupric ammonium complexes; chromium complexes, organic titanates, and dichromates; and the like. When required, a crosslinking agent usually is employed in an amount in the range of from about 1 to about 5 percent by weight, based on the weight of PVOH in the aqueous solution, although higher or lower amounts can be employed if desired.

In addition to the use of chemical crosslinking agents as discussed above, the formed PVOH film can be crosslinked by radiation, such as electron beam radiation, ultraviolet radiation, and the like. The formed PVOH film also can be crosslinked thermally by heating the film to a temperature in excess of 100 degrees C. The preferred temperature range is from about 120 to about 180 degrees C. In the preferred temperature range, the crosslinking time typically is about one hour. Thermal crosslinking is preferred over the inclusion of a chemical crosslinking agent in the coating solution, especially when the breathable barrier is to be used in a disposable absorbent article such as a diaper or sanitary napkin.

Because flexibility of the breathable barrier often is a required characteristic, it may be either necessary or desirable to include a plasticizer in the PVOH coating solution. Suitable plasticizers in general are any of the known plasticizers for PVOH, such as glycerol, the poly(oxyethylene) diols, pentaerythritol, 1,2,6-hexanetriol, sorbitol, formamide, urea, and the like. Glycerol has been found to be a particularly useful plasticizer and is preferred. Thus, a plasticizer can be present in an amount of from 0 to about 50 percent by weight, based on the weight of PVOH employed, although somewhat higher amounts perhaps can be used, depending upon the polymeric material and its molecular weight range. When employed with PVOH resins, the plasticizer preferably will be present in an amount of from about 15 to about 25 percent by weight.

Some care must be exercised in the use of plasticizers, however. While plasticizers can increase film flexibility and enhance film formation, they also can adversely affect the liquid water barrier characteristics of the breathable barrier, especially when used at unusually high levels. Thus, the plasticizer level in general should be kept to the minimum level which is consistent both with film formation and flexibility requirements and the desired properties of the breathable barrier.

As indicated hereinbefore, the PVOH or other water-soluble polymeric material preferably is applied to the porous sheet as an aqueous solution. Application usually is made at ambient temperature and pressure, although such conditions are not mandatory. Indeed, any combination of temperature and pressure can be employed, although for reasons of economics and convenience, ambient temperature and pressure are preferred. The concentration of polymeric material in the solution is not known to be critical and usually is a matter of convenience. In practice, when the polymeric material is PVOH, concentrations of from about 4 to about 12 percent by weight are typical. The preferred concentration range is from about 5 to about 10 percent by weight as employed in the examples.

The method of application is not known to be critical and largely is a matter of convenience. Thus, the PVOH solution can be applied by spraying, dipping, brushing, doctor blade, roller, Meyer rod, and the like. In addition, a single coat or multiple coats can be applied. Moreover, if multiple coats are applied, the application solution does not have to be the same for each application. The several solutions can utilize different concentrations of the same water-soluble polymeric material, the presence or absence of such compounds as crosslinking agent and plasticizer, different polymeric materials at the same or different concentrations, or combinations of any of the foregoing variations.

After the aqueous solution of water-soluble polymeric material has been applied to the porous sheet, the sheet is dried by removing water, preferable at an elevated temperature. The removal of water generally results in the formation of a film of the polymeric material. If a subsequent porous sheet is to be applied adjacent to the film, such application can be done before drying has been completed and is preferred in cases where the polymeric material has adhesive properties. If desired, multiple coatings of the polymeric material solution can be applied, with the last-applied coating serving as the adhesive layer.

Finally, additives other than crosslinking agents and plasticizers can be incorporated into the aqueous coating solution or film of polymeric material, if desired. Such additives include binders, extenders, fillers, pigments, dyes, defoamers, preservatives, fungicides, wetting agents, deodorants, fluorescent agents, and the like.

It may be noted at this point that the porous sheet can be a single layer or a composite of two or more layers. Moreover, the breathable barrier can be a composite of more than the two layers required by the present invention. Composite structures are, in fact, preferred since the use of multiple layers permits one to taylor the breathable barrier for any desired combination of barrier properties, including water vapor transmission rate, and aesthetic properties.

By way of illustration of multilayer constructions for the barrier, when the barrier is to be used as the baffle in a sanitary napkin, the barrier can be a composite of a thermally bonded carded web, a second layer as provided by the present invention, and a meltblown web first layer, with the meltblown web being the inner or body side layer. Alternatively, the bonded carded web can be replaced with a spunbonded web.

For disposable diaper or incontinent pad applications, an example of a suitable outer cover is a composite of a first meltblown web as the first layer, two layers of a film as provided by the present invention, a third layer of a film as provided by the present invention to serve as an adhesive for the next layer which is a second meltblown web, and a final layer which is a spunbonded web. Each meltblown web can have a basis weight of, for example 17 g/m$^2$, and the spunbonded web can have a basis weight of, for example, 23.8 g/m$^2$, with the spunbonded web being the outermost layer. That is, the first meltblown layer is placed next to the absorbent batt within the disposable diaper or incontinent pad. Of course, other constructions are possible and come within the spirit and scope of the present invention.

The present invention is further described by the examples which follow which illustrate certain preferred embodiments. Such examples are not to be construed as in any way limiting either the spirit or scope of the present invention. In the examples, all temperatures are in degrees Celsius and all amounts are in parts by weight, unless indicated otherwise.

In the examples, the water vapor transmission rate was determined in accordance with ASTM Method E 96-80, Standard Test Methods for Water Vapor Transmission of Materials, Procedure 12. The apparatus employed was a Vapometer (Catalog No. 68-1, Thwing-Albert Instrument Company, Philadelphia, Pa.). The apparatus consisted of a two-inch (about 5.1-cm) deep aluminum cup having a flanged top with a neoprene rubber gasket. The inner diameter of the flange was 2.5 inches (about 6.4 cm). About 100 ml of water was added to the cup and a sample of the breathable barrier to be tested was sealed mechanically over the open end of the cup and weighed. The sample-cup assembly was placed in an oven at 37 degrees C. and about 50 percent relative humidity. Periodic weighings of the sample-cup assembly permitted calculation of the water vapor transmission rate (WVTR).

The effectiveness of the coated porous sheet as a barrier to liquid water was measured by INDA Standard Test 80.7-70 (82), INDA Standard Test for Saline Repellency of Nonwovens, often referred to as the Mason Jar Test. The test liquid was 0.9 percent by weight saline solution. In both tests, the coated porous sheet was oriented inwardly, i.e., with the porous sheet closest to the saline solution.

EXAMPLE 1

An approximately five percent by weight aqueous solution of poly(vinyl alcohol) was prepared by dispersing the resin in water at ambient temperature and heating the mixture at about 96 degrees with moderate agitation until the resin dissolved. The poly(vinyl alcohol) employed was VINOL ® 165 (Air Products and Chemicals, Inc., Polymer Chemicals, Allentown, Pa.). According to information supplied by the manufacturer, the resin was in excess of 99.3 percent hydrolyzed and a 4 percent by weight aqueous solution of the resin at 20 degrees had a viscosity of 55–65 cps. The resulting solution then was allowed to cool to ambient temperature.

A polypropylene meltblown web sample having a nominal basis weight of about 34 g/m$^2$ and a measured basis weight of 38 g/m$^2$ was coated with the above PVOH solution by means of a brush. The coated sample was air dried overnight at ambient temperature. The poly(vinyl alcohol) add-on was 17 g/m². The coated sample passed the Mason Jar Test and gave a water vapor transmission rate of 1171 g/m²/24 hours. A comparable, uncoated sample having a nominal basis weight of about 34 g/m² gave a WVTR of 2518 g/m²/24 hours and failed the Mason Jar test.

EXAMPLE 2

The procedure of Example 1 was repeated six times at six different PVOH add-on levels. The results are summarized in Table 1.

TABLE 1

| Sample No. | Nom. Basis[a] | Meas. Basis[b] | PVOH Add-on[c] | Mason Jar Test | WVTR[d] |
|---|---|---|---|---|---|
| 2A | 34 | 36 | 4 | Passed | 2959 |
| 2B | 34 | 37 | 9 | Passed | 1277 |
| 2C | 34 | 31 | 31 | Passed | 1048 |
| 2D | 34 | 31 | 40 | Passed | 1183 |
| 2E | 34 | 31 | 58 | Passed | 978 |
| 2F | 34 | 39 | 151 | Passed | 742 |

[a]Nominal basis weight in g/m².
[b]Measured basis weight in g/m².
[c]In g/m².
[d]Water vapor transmission rate in g/m²/24 hours.

EXAMPLE 3

The procedure of Example 1 was repeated, except that the polypropylene meltblown web sample was replaced with polypropylene spunbonded web samples of varying basis weights. The results are summarized in Table 2.

TABLE 2

| Sample No. | Nom. Basis[a] | Meas. Basis[b] | PVOH Add-on[c] | Mason Jar Test | WVTR[d] |
|---|---|---|---|---|---|
| 3A | 34 | — | 0 | Failed | 2788 |
| 3B | 34 | — | 10 | Failed | 2000 |
| 3C | 34 | 40 | 12 | Failed | 2037 |
| 3D | 42 | — | 0 | Failed | 2927 |
| 3E | 42 | 41 | 13 | Failed | 2175 |
| 3F | 51 | — | 0 | Failed | 1990 |
| 3G | 51 | 44 | 13 | Failed | 2278 |
| 3H | 68 | — | 0 | Failed | 2798 |
| 3I | 68 | 64 | 12 | ND[e] | ND |

[a]Nominal basis weight in g/m².
[b]Measured basis weight in g/m² (not all samples were measured).
[c]In g/m².
[d]Water vapor transmission rate in g/m²/24 hours.
[e]Not determined.

The results of Examples 1-3, inclusive, demonstrate the fact that the PVOH film and the porous substrate upon which it is formed are interdependent. That is, choices regarding the nature of the aqueous PVOH coating solution are in part dependent upon the nature of the porous substrate to be coated. Meltblown webs are less porous than spunbonded webs at any given basis weight. Thus, the sizes of pores at the surfaces of spunbonded webs tend to be significantly larger than those of meltblown webs. Consequently, the thickness of the PVOH film joined to a spunbonded web in general needs to be substantially thicker than for a meltblown web of the same basis weight. The failure of coated spunbonded webs to pass the Mason Jar Test also is related to the ability of the PVOH resin to bridge the pores or openings at the surface of the porous substrate during the film-forming process. Adding a plasticizer to the PVOH resin usually has a positive effect on such bridging ability.

The next example is a repeat of Example 3, except that a plasticizer was included in the aqueous resin solution.

EXAMPLE 4

The procedure of Example 3 was repeated, except that the aqueous PVOH resin solution also contained approximately 1 percent by weight glycerol (25 percent by weight, based on the dry weight of the PVOH resin). The results are summarized in Table 3.

TABLE 3

| Sample No. | Nom. Basis[a] | Meas. Basis[b] | Film Add-On[c] | Mason Jar Test | WVTR[d] |
|---|---|---|---|---|---|
| 4A | 34 | — | 0 | Failed | 2788 |
| 4B | 34 | 42 | 57 | Passed | 1173 |
| 4C | 42 | — | 0 | Failed | 2927 |
| 4D | 42 | 50 | 54 | Passed | 739 |
| 4E | 51 | — | 0 | Failed | 1900 |
| 4F | 51 | 49 | 59 | Passed | 748 |
| 4G | 68 | — | 0 | Failed | 2798 |
| 4H | 68 | 71 | 52 | Passed | 742 |
| 4I | 102 | — | — | Failed | 2808 |
| 4J | 102 | 109 | 77 | Passed | 960 |

[a]Nominal basis weight in g/m².
[b]Measured basis weight in g/m².
[c]In g/m².
[d]Water vapor transmission rate in g/m²/24 hours.

Because the coated samples in Example 4 all had high levels of film add-on, it is difficult to determine to what extent the presence of a plasticizer contributed to the 100 percent Mason Jar Test pass rate observed in Example 4. Experience has shown, though, that the presence of a plasticizer greatly enhances the bridging ability of the resin during film formation and minimizes or eliminates cracks and holes in the formed film. However, the amount of plasticizer must be selected with some care, depending upon the application, as shown by Examples 5-8, inclusive.

EXAMPLE 5

The procedure of Example 1 was repeated twice, except that the PVOH solution also contained about 3.5 percent by weight glycerol, or about 76 percent by weight based on the weight of PVOH resin, and the PVOH solution was applied to the meltblown web by means of a No. 22 Meyer rod. The results obtained are summarized in Table 4.

TABLE 4

| Sample No. | Film Add-On[a] | Mason Jar Test | WVTR[b] |
|---|---|---|---|
| 5A | 8.3 | Failed | 2908 |
| 5B | 8.4 | Failed | 2521 |

[a]In g/m².
[b]Water vapor transmission rate in g/m²/24 hours.

While some water-soluble polymeric materials may be capable of withstanding the presence of as large an amount of plasticizer as was employed in Example 5, VINOL ® 165 does not appear to be one of them unless a crosslinking agent is added to impart additional film integrity. Moreover, the effect observed in Example 5 was not altered by placing the film between two porous substrates, as shown in the next three examples.

EXAMPLE 6

A meltblown polypropylene web having a nominal basis weight of about 34 g/m² was coated with resin solution of Example 5 by means of a No. 22 Meyer rod.

A spunbonded polypropylene web having a nominal basis weight of about 34 g/m² was immediately layed over the coated surface of the meltblown web. The resulting composite was air dried. The film add-on was 6.5 g/m². Three samples of the composite thus obtained were subjected to the Mason Jar Test; only one passed. The composite gave a water vapor transmission rate of 2471 g/m²/24 hours.

EXAMPLE 7

The procedure of Example 6 was repeated, except that the film add-on was 5.6 g/m². The resulting composite failed the Mason Jar Test and gave a water vapor transmission rate of 2534 g/m²/24 hours.

EXAMPLE 8

The procedure of Example 6 was repeated, except that the nominal basis weight of each of the two webs was 25 g/m² and the film add-on was 5.6 gm². The resulting composite failed the Mason Jar Test and gave a water vapor transmission rate of 2923 g/m²/24 hours.

EXAMPLE 9

The procedure of Example 1 was repeated, except that the PVOH resin was a mixture of 50 percent by weight VINOL ® 165 and 50 percent by weight VINOL ® 205 (Air Products and Chemicals, Inc. Polymer Chemicals, Allentown, Pa.) and the meltblown web sample was coated by means of a No. 22 Meyer rod. According to information supplied by the manufacturer, the VINOL ® 205 resin was 87.0–89.0 percent hydrolyzed and a 4 percent by weight aqueous solution of the resin at 20 degrees had a viscosity of 5–6 cps. The nominal basis weight of the web was 34 g/m² and the measured basis weight was 39 g/m². The PVOH add-on was 5.9 g/m². Two out of three samples of the composite passed the Mason Jar Test and the composite gave a water vapor transmission rate of 2095 g/m²/24 hours.

EXAMPLE 10

The procedure of Example 1 was repeated, except that different PVOH resins were employed, actual basis weights of the samples were not calculated, and the PVOH solution was applied by means of a Meyer rod. The characteristics of the several PVOH resins employed are summarized in Table 5, based on information provided by the manufacturer (Air Products and Chemicals, Inc., Polymer Chemicals, Allentown, Pa.), and the results obtained are summarized in Table 6.

TABLE 5

| Resin | Percent Hydrolyzed | Viscosity[a] |
| --- | --- | --- |
| VINOL ® 125 | 99.3 | 26–30 |
| VINOL ® 165 | 99.3 | 55–65 |
| VINOL ® 107 | 98.0–98.8 | 5.4–6.5 |
| VINOL ® 205 | 87.0–89.0 | 5–6 |

[a]In cps, of a 4 percent by weight aqueous solution at 20 degrees C.

TABLE 6

| Sample No. | Nom. Basis[a] | VINOL ® Resin | PVOH Add-On[b] | Mason Jar Test[c] | WVTR[d] |
| --- | --- | --- | --- | --- | --- |
| 10A | 34 | — | 0 | 0/3 | 3170 |
| 10B | 34 | 125 | 4 | 2/3 | 2366 |
| 10C | 34 | 165 | 4 | 2/3 | 2922 |
| 10D | 34 | 107 | 6 | 3/3 | 2004 |
| 10E | 34 | 205 | 4 | 3/3 | 2695 |
| 10F[e] | 34 | 205 | 4 | 2/3[f] | 2991 |

[a]Nominal basis weight in g/m².
[b]In g/m².
[c]Number of trials which passed/number of trials run.
[d]Water vapor transmission rate in g/m²/24 hours.
[e]Heat treated at 120 degrees C. for 80 minutes to thermally crosslink the PVOH.
[f]One trial leaked around the rim of the jar.

Sample 10E of Example 10 is of particular interest since it illustrates one of the unexpected results from using water-soluble polymeric materials in accordance with the present invention. Both the resin and the film formed from the resin are soluble in water at ambient temperature. Yet, the sample passed the Mason Jar test. In the test, the sample was oriented with the meltblown web toward the inside of the jar and, as a consequence, was in direct contact with the water. Because the meltblown web itself acts as a partial barrier to the passage of water through it, the web acts as a protective layer for the film and significantly extends the period of time over which the film can remain intact in the presence of water. Thus, the film and the porous substrate in combination can, depending upon the characteristics of the substrate, exhibit a kind of synergism in which the barrier properties of the combination exceed the barrier properties of the components of the combination. That is, the meltblown web by itself fails the Mason Jar Test, and the film by itself is soluble in water and would dissolve within the time period over which the test is run. In combination, however, the meltblown web and water-soluble film are able to pass the Mason Jar Test if oriented properly with respect to the direction of the aqueous challenge. Since such a resin may not be suitable for all applications, it is preferred that the continuous film portion of the barrier of the present invention have a somewhat reduced water solubility; that is, it is preferred that such film be substantially insoluble in water having a temperature less than about 50 degrees C.

EXAMPLE 11

The procedure of Example 1 was repeated, except that the coating solution was an eight percent by weight solution of VINOL ®125 in water, the meltblown web had a nominal basis weight of 25 g/m², and the coating solution was applied by means of a No. 22 Meyer rod. The coated sample was dried at about 140 degrees for two minutes. The PVOH add-on was 5.3 g/m². The sample passed the Mason Jar Test and gave a water vapor transmission rate of 1761 g/m²/24 hours.

EXAMPLE 12

The procedure of Example 11 was repeated, except that a second coating of the PVOH solution was applied over the first coating after the sample had been dried; the total PVOH add-on was 7.1 g/m². The sample passed the Mason Jar Test and gave a water vapor transmission rate of 1348 g/m²/24 hours.

EXAMPLE 13

The procedure of Example 11 was repeated, except that the PVOH solution was replaced with a 10 percent by weight aqueous solution of VINOL ® SH-72 (Air Products and Chemicals, Inc., Polymer Chemicals, Allentown, Pa.). According to information supplied by the manufacturer, the resin was a tackified (borated) grade derived from VINOL ®165. The viscosity of a 10 percent by weight aqueous solution of the resin at 25 degrees C. was reported to be 3800-5500 cps. The PVOH add-on was 7.7 g/m². The sample passed the Mason Jar Test and gave a water vapor transmission rate of 1714 g/m²/24 hours.

EXAMPLE 14

The procedure of Example 11 was repeated, except that the PVOH solution also contained 1 percent by weight glycerol, or about 12 percent by weight, based on the weight of PVOH. The add-on of the PVOH composition was 5.3 g/m². The sample passed the Mason Jar Test and gave a water vapor transmission rate of 2392 g/m²/24 hours.

The polypropylene meltblown web employed in Examples 11-14, inclusive, was examined by scanning electron microscopy. The coated samples obtained from Examples 11-14, inclusive, also were examined by scanning electron microscopy.

Figure 1:
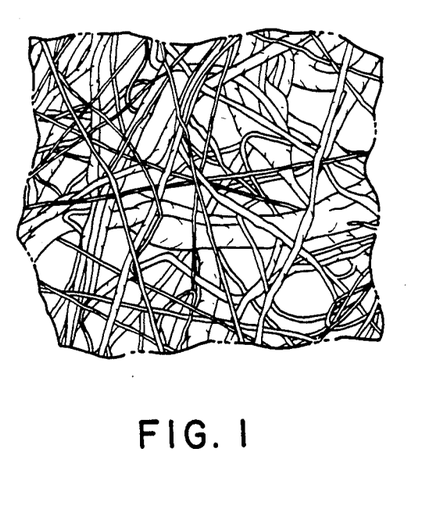
FIG. 1 is a representation of a plane view scanning electron micrograph, taken at a magnification of 200×, of a polypropylene meltblown nonwoven web having a nominal basis weight of 25 g/m$^2$, as employed in Examples 11-14, inclusive.

FIG. 1 is a representation of a plane view scanning electron micrograph (SEM) of the meltblown web used in Examples 11-14, inclusive, taken at a magnification of 200×. The porous nature of the web is clearly evident.

Figure 2:
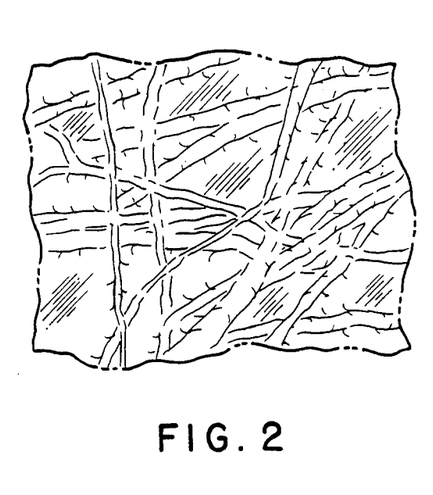
FIG. 2 is a representation of a plane view scanning electron micrograph of a polypropylene meltblown nonwoven web coated in accordance with the present invention as described in Example 13, taken of the coated side at a magnification of 200×.

FIG. 2 is a representation of a plane view SEM of the coated sample of Example 13, taken at a magnification of 200×. The continuous nature of the film and the comingling phenomenon described earlier are apparent.

Figure 3:
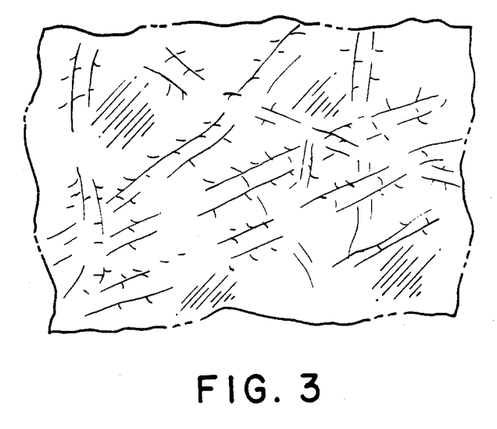
FIG. 3 is a representation of a plane view scanning electron micrograph of a polypropylene meltblown nonwoven web coated twice on the same side in accordance with the present invention as described in Example 12, taken at a magnification of 200×, in which the coating is a tackified poly(vinyl alcohol).
Figure 4:
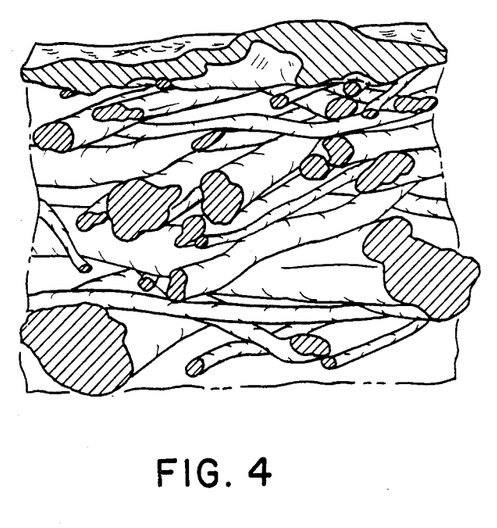
FIG. 4 is a representation of a cross-sectional view scanning electron micrograph of a polypropylene meltblown nonwoven web coated in accordance with the present invention as described in Example 11, taken at a magnification of 1000×.
Figure 5:
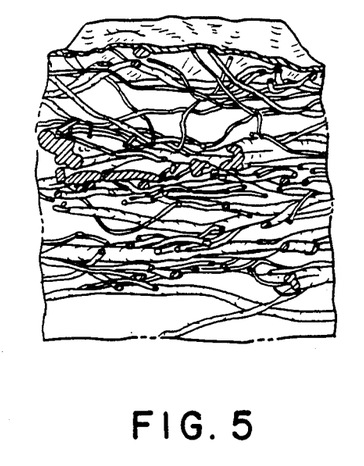
FIG. 5 is a representation of a cross-sectional view scanning electron micrograph of a polypropylene meltblown nonwoven web coated in accordance with the present invention as described in Example 14, taken at a magnification of 200×, in which the coating is a plasticized poly(vinyl alcohol).
Figure 6:
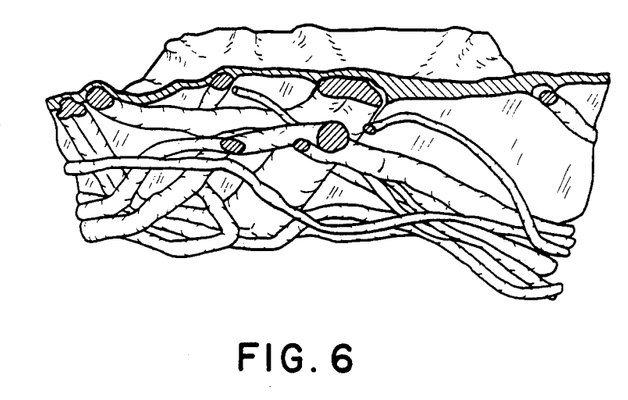
FIG. 6 is the same as FIG. 5, except that the magnification is 1000×.
Figure 7:
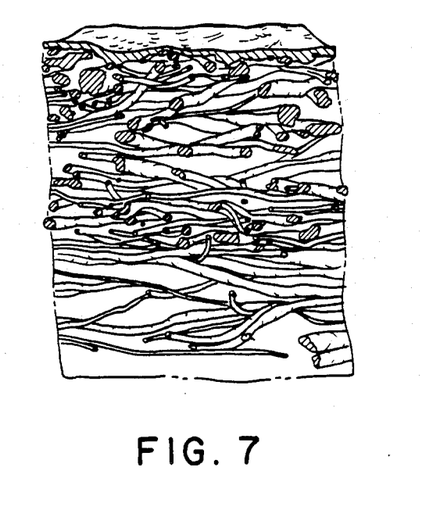
FIG. 7 is a representation of a cross-sectional view scanning electron micrograph of a polypropylene meltblown nonwoven web coated in accordance with the present invention as described in Example 13, taken at a magnification of 200×, in which the coating is a tackified poly(vinyl alcohol).
Figure 8:
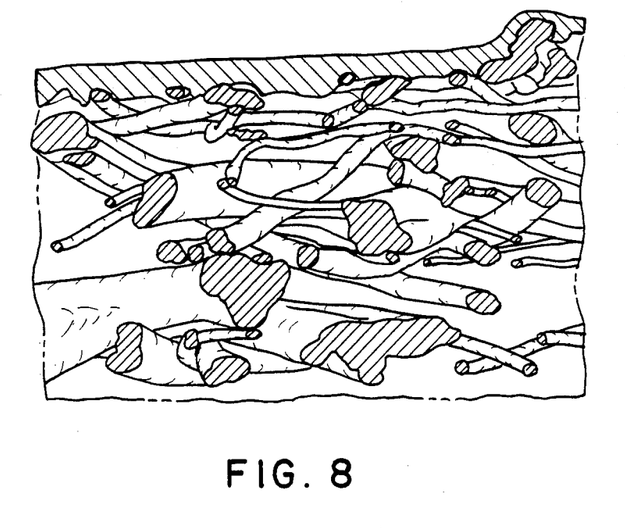
FIG. 8 is the same as FIG. 7, except that the magnification is 1000×.

FIG. 3 is similar to FIG. 2, except that the sample is that of Example 12. The effectiveness of two coats in giving a much more substantial film is apparent, even though the total film add-on is about the same for both samples.

FIGS. 4-8, inclusive, are representations of cross-sectional view SEMs of the coated samples of Examples 11, 13, and 14, taken at either of two magnifications, as summarized in the following table:

| FIG. | Magnification | Example |
|---|---|---|
| 4 | 1000× | 11 |
| 5 | 200× | 14 |
| 6 | 1000× | 14 |
| 7 | 200× | 13 |
| 8 | 1000× | 13 |

The figures illustrate the very thin nature of the resulting films and the comingling phenomenon described earlier.

EXAMPLE 15

A 1.5-mil poly(vinyl alcohol) film was edge-bonded thermally to a meltblown polypropylene web having a basis weight of 25 gsm. Edge bonding was accomplished with a Model 14P Thermal Impulse Heat Sealing Machine (Vertrod Corp., Brooklyn, N.Y.); both the dwell and heat settings were about 4. The film was a MONO-SOL 1-000 series film (Mono-Sol Division, Chris Craft Industries, Inc, Gary, Ind.) having a water vapor transmission rate of 1719 g/m²/24 hours. A spunbonded polypropylene web then was thermally bonded to the other side of the film. The resulting composite passed the Mason Jar Test, and gave a water vapor transmission rate of 1780 g/m²/24 hours.

Having thus described the invention, numerous changes and modifications thereof will be readily apparent to those having ordinary skill in the art without departing from the spirit or scope of the invention.

What is claimed is:

1. A breathable barrier which comprises:
   A. a first layer which is a porous sheet having a first side and a second side; and
   B. a second layer joined to said first side of said first layer, which second layer comprises a continuous film of a water-soluble polymeric material, in which:
      said film is not microporous in that it is substantially free of voids which connect the two surfaces of said film;
      water molecules are capable of being transported through the thickness of said film as a result of the solubility of said water molecules in said polymeric material; and
      said film has an average thickness of from about 3 to about 250 microns;
   wherein the first layer side of said second layer is intimately comingled with at least some of the fibers at the surface of said first side of said first layer, none of the pores at the surface of said first side of said first layer are so large as to significantly adversely affect the barrier properties of said breathable barrier as a consequence of said comingling, and said breathable barrier has a water vapor transmission rate at 37 degrees C. and about 50 percent relative humidity of from about 100 to about 5,000 g/m²/24 hours and is impermeable to 0.9 percent by weight saline solution at about 21 degrees C. for a period of at least about one hour at a hydrostatic head of at least about 11.4 cm.

2. The breathable barrier of claim 1, in which said film is substantially insoluble in water having a temperature less than about 50 degrees C.

3. The breathable barrier of claim 1, in which said porous sheet is a nonwoven web.

4. The breathable barrier of claim 1, in which said nonwoven web is a spunbonded web.

5. The breathable barrier of claim 4, in which said spunbonded web is comprised of polyolefin fibers.

6. The breathable barrier of claim 5, in which said polyolefin fibers are polypropylene.

7. The breathable barrier of claim 5, in which said polyolefin fibers are polyethylene.

8. The breathable barrier of claim 3, in which said nonwoven web is a meltblown web.

9. The breathable barrier of claim 8, in which each of at least about 50 percent of the pores at the surface of said first side of said first layer has a cross-sectional area of less than about $3.2 \times 10^{-8}$ m².

10. The breathable barrier of claim 8, in which essentially none of the pores at the surface of said first side of said first layer has a cross-sectional area in excess of about $3.2 \times 10^{-8}$ m².

11. The breathable barrier of claim 8, in which said meltblown web is comprised of polyolefin fibers.

12. The breathable barrier of claim 11, in which said polyolefin fibers are polypropylene.

13. The breathable barrier of claim 11, in which said polyolefin fibers are polyethylene.

14. The breathable barrier of claim 3, in which said nonwoven web is a coformed web consisting of primary web-forming fibers and secondary fibers or particles dispersed therein.

15. The breathable barrier of claim 14, in which said primary fibers are a polyolefin.

16. The breathable barrier of claim 15, in which said polyolefin primary fibers are polypropylene.

17. A breathable barrier which comprises a porous sheet laminated on at least one side to a film of a water-soluble polymeric material, in which:
said film is not microporous in that it is substantially free of voids which connect the two surfaces of said film;
water molecules are capable of being transported through the thickness of said film as a result of the solubility of said water molecules in said polymeric material; and
said film has an average thickness of from about 3 to about 250 microns;
wherein said breathable barrier has a water vapor transmission rate at 37 degrees C. and about 50 percent relative humidity of from about 100 to about 5,000 g/m²/24 hours and is impermeable to 0.9 percent by weight saline solution at about 21 degrees C. for a period of at least about one hour at a hydrostatic head of at least about 11.4 cm.

18. The breathable barrier of claim 17, in which said film is substantially insoluble in water having a temperature less than about 50 degrees C.

19. The breathable barrier of claim 17, in which said porous sheet is a nonwoven web.

20. The breathable barrier of claim 19, in which said nonwoven web is a spunbonded web.

21. The breathable barrier of claim 20, in which said spunbonded web is comprised of polyolefin fibers.

22. The breathable barrier of claim 21, in which said polyolefin fibers are polypropylene.

23. The breathable barrier of claim 21, in which said polyolefin fibers are polyethylene.

24. The breathable barrier of claim 19, in which said nonwoven web is a meltblown web.

25. The breathable barrier of claim 24, in which said meltblown web is comprised of polyolefin fibers.

26. The breathable barrier of claim 25, in which said polyolefin fibers are polypropylene.

27. The breathable barrier of claim 25, in which said polyolefin fibers are polyethylene.

28. The breathable barrier of claim 19, in which said nonwoven web is a coformed web consisting of primary web-forming fibers and secondary fibers or particles dispersed therein.

29. The breathable barrier of claim 28, in which said primary fibers are polyolefin.

30. The breathable barrier of claim 29, in which said polyolefin primary fibers are polypropylene.

31. The breathable barrier of claim 1, in which said water-soluble polymeric material is a synthetic water-soluble polymeric material.

32. The breathable barrier of claim 31, in which said synthetic water-soluble polymeric material is a poly(vinyl alcohol).

33. The breathable barrier of claim 32, in which said porous sheet is a nonwoven web.

34. The breathable barrier of claim 33, in which said nonwoven web is a spunbonded web.

35. The breathable barrier of claim 34, in which said spunbonded web is comprised of polyolefin fibers.

36. The breathable barrier of claim 35, in which said polyolefin fibers are polypropylene.

37. The breathable barrier of claim 35, in which said polyolefin fibers are polyethylene.

38. The breathable barrier of claim 33, in which said nonwoven web is a meltblown web.

39. The breathable barrier of claim 38, in which each of at least about 50 percent of the pores at the surface of said first side of said first layer has a cross-sectional area of less than about $3.2 \times 10^{-8}$ m².

40. The breathable barrier of claim 38, in which essentially none of the pores at the surface of said first side of said first layer has a cross-sectional area in excess of about $3.2 \times 10^{-8}$ m².

41. The breathable barrier of claim 38, in which said meltblown web is comprised of polyolefin fibers.

42. The breathable barrier of claim 41, in which said polyolefin fibers are polypropylene.

43. The breathable barrier of claim 41, in which said polyolefin fibers are polyethylene.

44. The breathable barrier of claim 33, in which said nonwoven web is a coformed web consisting of primary web-forming fibers and secondary fibers or particles dispersed therein.

45. The breathable barrier of claim 44, in which said primary fibers are polyolefin.

46. The breathable barrier of claim 45, in which said polyolefin primary fibers are polypropylene.

47. The breathable barrier of claim 17, in which said water-soluble polymeric material is a synthetic water-soluble polymeric material.

48. The breathable barrier of claim 47, in which said synthetic water-soluble polymeric material is a poly(vinyl alcohol).

49. The breathable barrier of claim 48, in which said porous sheet is a nonwoven web.

50. The breathable barrier of claim 49, in which said nonwoven web is a spunbonded web.

51. The breathable barrier of claim 50, in which said spunbonded web is comprised of polyolefin fibers.

52. The breathable barrier of claim 51, in which said polyolefin fibers are polypropylene.

53. The breathable barrier of claim 51, in which said polyolefin fibers are polyethylene.

54. The breathable barrier of claim 49, in which said nonwoven web is a meltblown web.

55. The breathable barrier of claim 54, in which said meltblown web is comprised of polyolefin fibers.

56. The breathable barrier of claim 55, in which said polyolefin fibers are polypropylene.

57. The breathable barrier of claim 55, in which said polyolefin fibers are polyethylene.

58. The breathable barrier of claim 49, in which said nonwoven web is a coformed web consisting of primary web-forming fibers and secondary fibers or particles dispersed therein.

59. The breathable barrier of claim 58, in which said primary fibers are polyolefin.

60. The breathable barrier of claim 59, in which said polyolefin primary fibers are polypropylene.

61. A multilayered absorbent article in which at least one layer is the breathable barrier of claim 1.

62. The absorbent article of claim 61, in which said absorbent article is a disposable diaper.

63. The absorbent article of claim 61, in which said absorbent article is a sanitary napkin.

64. The absorbent article of claim 61, in which said absorbent article is an incontinent pad.

65. A multilayered absorbent article in which at least one layer is the breathable barrier of claim 8.

66. The absorbent article of claim 65, in which said absorbent article is a disposable diaper.

67. The absorbent article of claim 65, in which said absorbent article is a sanitary napkin.

68. The absorbent article of claim 65, in which said absorbent article is an incontinent pad.

69. A multilayered absorbent article in which at least one layer is the breathable barrier of claim 9.

70. A multilayered absorbent article in which at least one layer is the breathable barrier of claim 10.

71. A multilayered absorbent article in which at least one layer is the breathable barrier of claim 11.

72. A multilayered absorbent article in which at least one layer is the breathable barrier of claim 17.

73. The absorbent article of claim 72, in which said absorbent article is a disposable diaper.

74. The absorbent article of claim 72, in which said absorbent article is a sanitary napkin.

75. The absorbent article of claim 72, in which said absorbent article is an incontinent pad.

76. A multilayered absorbent article in which at least one layer is the breathable barrier of claim 24.

77. The absorbent article of claim 76, in which said absorbent article is a disposable diaper.

78. The absorbent article of claim 76, in which said absorbent article is a sanitary napkin.

79. The absorbent article of claim 76, in which said absorbent article is an incontinent pad.

80. A multilayered absorbent article in which at least one layer is the breathable barrier of claim 32.

81. The absorbent article of claim 80, in which said absorbent article is a disposable diaper.

82. The absorbent article of claim 80, in which said absorbent article is a sanitary napkin.

83. The absorbent article of claim 80, in which said absorbent article is an incontinent pad.

84. A multilayered absorbent article in which at least one layer is the breathable barrier of claim 38.

85. The absorbent article of claim 84, in which said absorbent article is a disposable diaper.

86. The absorbent article of claim 84, in which said absorbent article is a sanitary napkin.

87. The absorbent article of claim 84, in which said absorbent article is an incontinent pad.

88. A multilayered absorbent article in which at least one layer is the breathable barrier of claim 48.

89. The absorbent article of claim 88, in which said absorbent article is a disposable diaper.

90. The absorbent article of claim 88, in which said absorbent article is a sanitary napkin.

91. The absorbent article of claim 88, in which said absorbent article is an incontinent pad.

* * * * *